United States Patent [19]

Banker et al.

[11] Patent Number: 5,414,079
[45] Date of Patent: May 9, 1995

[54] OXIDIZED CELLULOSE

[75] Inventors: Gilbert S. Banker, Iowa; Vijay Kumar, Coralville, both of Iowa

[73] Assignee: Biocontrol Incorporated, Iowa City, Iowa

[21] Appl. No.: 101,184

[22] Filed: Aug. 3, 1993

[51] Int. Cl.⁶ ............................................. C08B 11/00
[52] U.S. Cl. ....................................... 536/56; 536/84; 536/120; 536/124
[58] Field of Search .................... 536/56, 84, 120, 124

[56] References Cited

U.S. PATENT DOCUMENTS

| | | | |
|---|---|---|---|
| 3,364,200 | 1/1968 | Ashton et al. | 536/56 |
| 3,627,676 | 12/1971 | Eccles, Jr. | 210/11 |
| 4,056,400 | 11/1977 | Diamantoglou et al. | 536/56 |
| 4,143,034 | 3/1979 | Jefferies et al. | 536/56 |
| 4,359,322 | 11/1982 | Neal et al. | 8/532 |
| 4,376,729 | 3/1983 | Crounse | 548/320 |
| 4,473,193 | 11/1988 | Pensa | 8/102 |
| 4,480,089 | 10/1984 | Chen et al. | 536/56 |
| 4,675,389 | 6/1987 | Cook et al. | 534/883 |

OTHER PUBLICATIONS

Clibbens et al "The Chemical Analysis of Cotton, The Rate of Oxycellulose Formation" Journal of the Textile Institute, vol. XVIII, 1927, pp. TI35–TI67.

*Primary Examiner*—Nathan M. Nutter
*Attorney, Agent, or Firm*—Cooper & Dunham

[57] ABSTRACT

A method for making an oxidized cellulose product from a cellulose material is disclosed. The method involves oxidizing a cellulose material into an oxidized cellulose product, comprising treating the cellulose material with a hypochlorite solution having an active chlorine content of between about 4 and about 6%, at a pH exceeding 9.5 and at a temperature, and for a time, effective to convert the cellulose material into the oxidized cellulose product; filtering the oxidized cellulose product; and washing the oxidized cellulose product with an antichlor agent such as sodium thiosulfate to remove chlorine and to raise the oxidized cellulose product to a neutral pH.

The oxidized cellulose product may be used to form films, dispersions, gels, as carriers, for pharmaceuticals, cosmetics and other products.

21 Claims, 2 Drawing Sheets

OXIDIZED CELLULOSE

OXIDIZED CELLULOSE

FIELD OF THE INVENTION

This invention relates to oxidized celluloses, and more particularly to oxidized celluloses connected by treatment with a hypochlorite solution.

BACKGROUND OF THE INVENTION

Oxidized celluloses (or oxycelluloses) are water insoluble materials produced by reacting cellulose with an oxidant such as gaseous chlorine, hydrogen peroxide, peracetic acid, chlorine dioxide, nitrogen dioxide (dinitrogen tetraoxide), persulfates, permanganate, dichromate-sulfuric acid hypochlorous acid, hypochlorous acid, hypohalites or periodates. These oxidized celluloses may contain carboxylic, aldehyde, and/or ketone functionalities, in addition to the hydroxyl groups, depending on the nature of the oxidant and the reaction conditions used in their preparation.

The treatment of cellulose with alkali and alkaline earth metal hypochlorites has been studied to establish conditions that prevent damage of cellulose fibers during various industrial processes involving or modifying grade cellulose products. Working with different grades of cotton cellulose fabrics, Clibbens et al. *J. Textile Inst.*, *18,* T135 (1927) note that the oxidation of cellulose by hypochlorite occurs more rapidly at a neutral pH, and in the presence of high concentrations of alkali (i.e., about 2–5N sodium hydroxide), than under mild acidic or basic conditions. The rapid increase in the oxidation rate with an increase in the alkali concentration is attributed to the increased mercerizing action of the sodium hydroxide. According to M. Lewin and J. A. Epstein J. Polymer Sci., 58,991 and 1023 (1962), the amount of carboxylic groups in the product decreases, whereas the aldehyde and ketone contents of the product increase with a decrease in the pH of the reaction mixture (from a pH of 10 to pH 5). Other studies indicate that oxidized cellulose products prepared under mild acidic conditions degrade and turn yellow during storage, whereas those prepared under basic conditions are quite stable [see T. P. Nevell, in Cellulose Chemistry and its Applications: 1. Cellulose, T. P. Nevell et al., eds., Ellis Hardwood Ltd., England (1985) at Ch, 10.].

U.S. Pat. No. 3,111,513 discusses the preparation of mixed carboxylic and aldehyde containing oxidized cellulose derivatives by reacting cellulose crystalline aggregates, prepared by treatment of the original cellulose material with 2.5N hydrochloric acid at boiling temperature for 15 minutes, with aqueous sodium hypochlorite solution at pH 7 and 9. The product of the reaction at pH 9 contained a higher carboxylic and a lower aldehyde content than the product formed at pH 7.0. The starting crystalline cellulose material had a level-off degree of polymerization value of 220.

The preparation of oxidized celluloses suitable for use as carrier vehicles in the development of cosmetic and pharmaceutical preparations, using alkali metal or alkaline earth metal hypohalites, is discussed in U.S. Pat. No. 4,480,089. The method involves treating a fibrous cellulosic material with a hypochlorite solution having an initial pH of about 12, at a temperature of 15°–60° C., and allowing the pH to drop to about 2. The method appears to produce mixed carbonyl containing oxidized cellulose derivatives. The products thus tend to change color and rapidly change color during storage in the presence of amine drugs.

Accordingly, an object of the present invention is to provide a method whereby a stable oxidized cellulose product, can be prepared from cotton linters, wood pulp and like materials. Another object is to produce an oxidized cellulose product stable to color change during storage, and compatible with a wide variety of chemicals and drugs.

A further objective of the present invention is to provide an oxidized cellulose material suitable for use as an excipient for preparing solid and semi-solid formulations having applications in cosmetic, pharmaceutical, agricultural, and consumer products development.

SUMMARY OF THE INVENTION

The invention provides a method of oxidizing a cellulose material into an oxidized cellulose product, comprising treating the cellulose material with a hypochlorite solution having an active chlorine content of between about 4 and 5.5%, at a pH exceeding 9.5 and at a temperature, and for a time, effective to convert the cellulose material into the oxidized cellulose product; filtering the oxidized cellulose product; and washing the oxidized cellulose product with an antichlor agent such as sodium thiosulfate to remove chlorine and to raise the oxidized cellulose product to a neutral pH. The oxidized cellulose product is additionally rinsed with methanol or acetone. The pH of the reaction mixture ranges from about 9.5 to about 14, and preferably the initial pH of the hypochlorite solution is about 13.5 to 14. The pH of the reaction mixture should exceed 9.5 throughout the oxidation step.

The weight to volume ratio of cellulose to hypochlorite solution should exceed 1:>5, but preferably ranges from about 1:7.5 to about 1:15, and the cellulose material may be cotton linters, α-cellulose, wood cellulose, or purified wood cellulose. The effective temperature for the reaction ranges from about 25° to about 90° C. Preferably, the effective temperature ranges from about 70° to about 80° C.

In another embodiment, the invention provides a method of oxidizing a cellulose material into an oxidized cellulose product, comprising: reacting the cellulose material with a hypochlorite solution having an active chlorine content of between about 4% and 6%, at a temperature ranging from about 60° C. to about 80° C., and a pH ranging from about 9.5 to about 14 for a period of time effective to convert the cellulose material into the oxidized cellulose product; isolating the oxidized cellulose product by filtration; washing the oxidized cellulose product in an aqueous solution of an antichlor agent such as sodium thiosulfate followed by rinsing the oxidized cellulose product with water to a neutral pH, and finally with methanol or acetone.

In yet another embodiment, the invention provides a method of forming a stable colloidal dispersion or near colloidal dispersion, comprising: agitating the oxidized cellulose product in water using a mechanical stirrer, and a dispersion optionally in the form of a thixotropic gel made in accordance with this method. The dispersion may additionally comprise an effective but minor amount of a preservative or a plasticizer.

In still further embodiments, the oxidized cellulose product of the present invention (made in accordance with the inventive process) or dispersion thereof may form part of a film forming agent or a pharmaceutical carrier.

The invention also provides a composition of matter comprising a major amount of a carrier including the oxidized cellulose product of the present invention or a dispersion thereof in water, and a minor but effective amount of an active ingredient selected from the group consisting of a cosmetic, a pharmaceutical agent, a pesticide, a fungicide, a fragrance, and a pigment.

BRIEF DESCRIPTION OF THE DRAWINGS

Further features and advantages of the invention will become apparent to those skilled in the art upon reviewing the following detailed description of the embodiments together with the appended drawings in which.

DETAILED DESCRIPTION OF THE EMBODIMENTS

Figure 1:
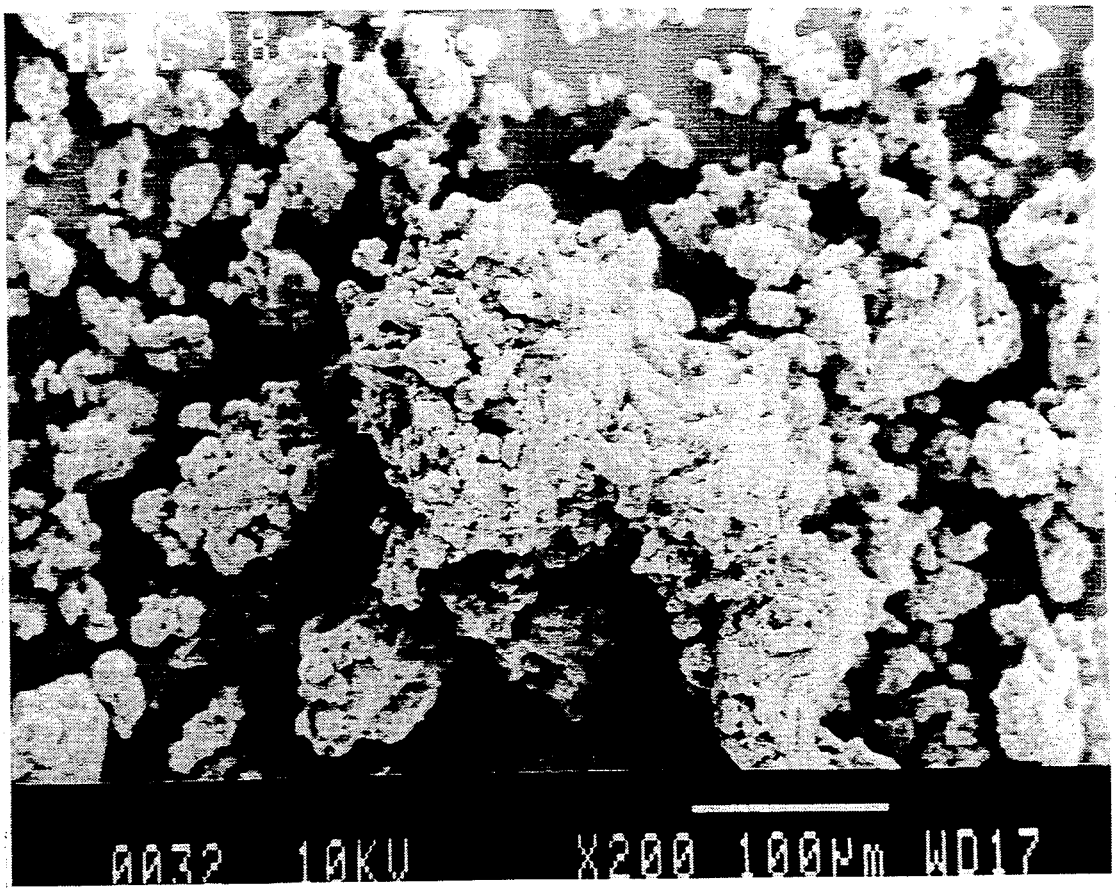
FIG. 1 is a scanning electron photomicrograph (200X) of oxidized cellulose product made in accordance with the present invention.

The present invention thus provides a method whereby a cellulose material such as cotton linters, $\alpha$-cellulose, wood pulp, purified wood pulp, and the like, can be readily and economically converted into a stable oxidized cellulose product by treatment with a hypochlorite solution, under controlled high pH conditions (preferably between pH 9.5–14). The reaction can be carried out at a temperature ranging from 25° C. to 90° C. (preferably between 70° C. and 80° C.). The present oxidized cellulose product can be readily isolated as a fine powder, or converted into friable aggregates or into an aqueous dispersion.

The method uses a hypochlorite solution of sufficient alkalinity to maintain a high controlled alkaline pH condition (i.e., above pH 9.5) throughout the oxidation cycle. This high pH eliminates the need of periodic additions of alkali solution to the reaction mixture to maintain the alkaline pH conditions. By conducting the entire reaction under alkaline conditions, a more stable product results, which retains a pure white color over extended period of time, and is compatible with a wide range of chemicals and drugs, which is essential in the application fields of interest.

The present oxidized cellulose product readily disperses in water and forms thixotropic dispersions. Such suspensions/dispersions, which may be optionally combined with other pharmaceutical and cosmetic adjuvants, can be used for producing novel film-forming systems. A wide variety of solid (crystalline or amorphous) and liquid (volatile or non-volatile) acidic, neutral, and basic bioactive compounds can be entrapped/loaded in such systems, thereby producing substantive controlled and/or sustained release formulations, having unique applications in the development of variety of cosmetic, pharmaceutical, agricultural, and consumer products. Topical formulations (cream, lotion, or spray) prepared using the present oxidized cellulose material, are bioadhesive, can be applied on the human skin or hair, can be included in cosmetics. They may be formulated without fats, waxes, oils or surfactants, unlike conventional cosmetic and topical vehicles, thereby producing hypoallergenic and non-irritating systems. Advantageously, they are entirely natural in origin.

Appropriately plasticized aqueous dispersions of the present oxidized cellulose product, optionally including other ingredients, can be used to develop drug-containing transdermal patches. The dispersions may also be designed as spray systems, aerosols, lotions, or creams. The systems may be loaded with fragrance oils or other active ingredients such as acaracides or insect repellents, skin protective agents including sunscreen agents, and a wide variety of drugs. When applied to the skin, vehicles made in accordance with the present invention have the ability to produce monolithic topical films, able to produce controlled drug or chemical agent release into the skin, or to the environment (volatile agent release to the air). The product in its powder form can also be used in the preparation of controlled and/or sustained release oral dosage forms (e.g., as a diluent, binder and/or disintegrant in the making of tablets).

Aqueous hypochlorite solutions are known to be stable at room temperature and under strongly alkaline conditions. At elevated temperatures, the hypochlorite ions, however, disassociate and produce chloride and chlorate ions. The latter slowly liberates oxygen. Since the reaction between cellulose and alkali metal chlorate does not appear to produce the desired oxidized cellulose product, the formation of the present product may occur as a result of he attack by the hypochlorite ions only. The non-fibrous nature of the product results from the concurrent cleavage of the $\beta$-1, 4-glycosidic linkages.

The present method involves reacting a cellulosic material with a hypochlorite solution having an initial pH between 13.0 to 14, and an active chlorine content between about 4–6% (preferably about 5.0%). Hypochlorite solutions containing higher percentage chlorine content (i.e., higher than 5.5%) can also be used, but such solutions are less preferred because these solutions tend to deteriorate relatively rapidly during storage. The weight-to-volume ratio of cellulosic material to sodium hypochlorite solution is about 1:5.0–20.0, preferably about 1:7.5–15.0. The reaction mixture is then heated at about 45°–90° C., preferably about 70°–80° C., for a period of time sufficient to render complete rupturing of the starting cellulosic fibers into a fine powder. The pH of the reaction mixture remains above 9.5 throughout the oxidation cycle. The present oxidized cellulose product can also be prepared at temperatures lower than 45° C., but the reaction is very slow and it takes several days to weeks for completion. Therefore, such lower temperatures are not preferred for the practice of the present method.

The preferred method of the invention uses a hypochlorite solution of sufficient alkalinity that maintains the pH of the reaction medium above 9.5 throughout the oxidation cycle, ensures the occurrence of the same type of oxidation mechanism, mediated predominantly by the hypochlorite ions, and thereby producing a homogenous oxidized cellulose product which is stable and compatible with a wide variety of chemical drugs.

The preferred starting cellulosic material for the preparation of the present product is cotton linters (sheet or pulp). Other cellulosic materials that can be used include $\alpha$-cellulose, wood cellulose, purified wood cellulose, and the like. The hypochlorite solution may contain other counter cations such as potassium, calcium, or magnesium, instead of sodium ions. Alkali and alkaline earth metal hypobromites can also be used, but are less preferred.

The typical preparative method involves heating a cellulosic material in an appropriate volume of hypochlorite solution at 70°–80° C., with occasional agitation, until a fine white powder of the product is formed. The product can be isolated by filtration, followed by washing first with an aqueous solution of an antichlor agent (e.g., sodium thiosulfate) and then with water until the filtrate showed a neutral pH. If a dried powder is sought, the wet cake is washed with a water miscible organic solvent such as methanol or acetone, and is finally dried at room temperature or in an oven at temperatures below 45° C. Alternatively, the wet cake can be converted into an aqueous dispersion and then spray dried to produce a fine powder of the product. The wet cake may also be employed as a concentrate, thereby avoiding the drying step, for subsequent dilution as a topical vehicle, coating vehicle, or for other purposes. The yield of the product is about 60–80%.

It is observed that during the final stages of the washing with water (i.e., very near to the neutral pH), the product converts into a colloidal or semi-colloidal state, causing the filtration step to be very slow. This can be prevented by washing the solid, during the final stages, first with a mixed water-alcohol or water-acetone solvent system, and finally with anhydrous acetone.

A scanning electron micrograph (magnification X200) of the oxidized cellulose product prepared using a 1:7.5 weight-to-volume ratio of cotton linters and 5% hypochlorite solution, is shown in FIG. 1. As is evident from FIG. 1, the product is a highly aggregated powder consisting of particles ranging in size from as low as 1.0μ.

The present product hydrates readily in water and forms a thixotropic gel. The aqueous colloidal or near colloidal thixotropic dispersion can be readily prepared by suspending and homogenizing the hydrated material using a conventional laboratory mechanical stirrer or a homogenizer, or a household blender. The viscosity of the aqueous dispersion increases with an increase in the oxidized cellulose content. Aqueous dispersions containing about 15% or higher weight percentage of the product are creams to heavy pastes, whereas dispersions comprising more than 3% and less than 15% of the product are thixotropic lotions. Aqueous dispersions containing less than 3% product can be stabilized using minor, but effective amount(s) of one or more suspending agent(s) such as microcrystalline cellulose, smectite clays, fumed silicas, or modified clays. Any appropriate viscosity enhancing agents such as methyl cellulose, hydroxypropylcellulose, hydroxypropylmethylcellulose, carboxymethylcellulose, polyvinylpyrrolidones, polyacrylates, alginates, or the like, can also be used. A surfactant such as polysorbate, poloxamer, sorbitan mono acid ester (e.g., sorbitan monolaurate, sorbitan monooleate, etc.), sodium lauryl sulfate, or other non-toxic FDA accepted material, can also be used to assist formation of the dispersions. The present product also forms stable dispersions in hydroalcoholic systems (i.e., water-alcohol mixtures).

Although the aqueous dispersions of the present product are microbiologically stable at room temperature for several months, it is preferred to add minor, but effective amounts of one or more of the commonly used preservatives such as phenols, benzoates, parabens, quats (quaternium-15) and the like, to increase resistance and/or inhibition of any microbial growth.

Figure 2:
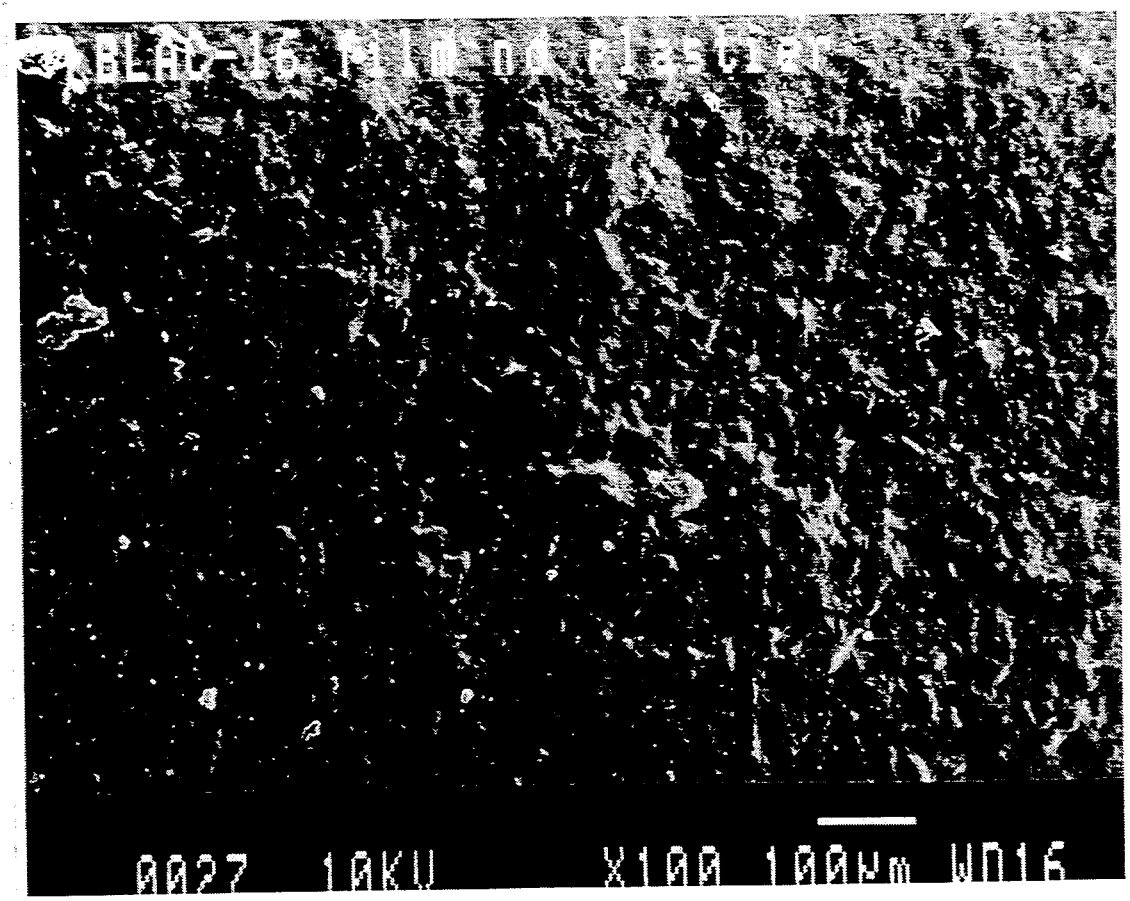
FIG. 2 is a scanning electron photomicrograph of a film prepared using an aqueous dispersion of the oxidized cellulose product made in accordance with the present invention on a Teflon coated metal surface.

Irrespective of the amount present, the aqueous dispersions of the present product form extremely adhesive white to clear films on the skin and on hair, and on a variety of other surfaces such as glass, metal, wood and the like. A scanning electron micrograph of the film prepared using an aqueous dispersion of the product on a Teflon coated metal surface, is shown in FIG. 2. If desired, minor but effective amounts of glycerin, propylene glycol, N,N-m- diethyltoluamide, mineral oil, citric acid esters, or the like can be used to plasticize the films. Appropriately plasticized dispersions rub-in smoothly on the human skin and readily dry to form uniform, flexible non-tacky, transparent, and non-oily films.

A wide variety of acidic, basic, and neutral drugs/chemicals, whether amorphous or crystalline solids or volatile or non-volatile liquid/oils, can be entrapped/loaded in such film forming systems. Chemicals containing free amino groups such as benzocaine, phenylpropanolamine, and the like, can also be used.

The present oxidized cellulose product is compatible with a wide variety of water soluble and water insoluble cosmetic and pharmaceutical excipients. For example, polymers such as methyl cellulose, hydroxypropylcellulose, hydroxypropylmethylcellulose, carboxymethylcellulose, polyvinylpyrrolidones, polyacrylates, alginates, microcrystalline cellulose, bentonite, smectite clays, fumed silicas, modified clays, and the like, and wetting and/or solubilizing agents such as polysorbates, poloxomers, polyoxyl ethers and esters, sodium lauryl sulfate, and the like, can all be used. These materials can be added directly to the dispersion, or mixed with the powdered oxidized cellulose product first and then converted into dispersion by stirring or homogenization in an appropriate amount of water, or separately dissolved or dispersed in water and then added to the cellulose dispersion. Water miscible organic solvents such as ethanol, isopropanol, and the like can be added to such dispersions, without affecting their physical state.

Drug and chemical containing aqueous and hydroalcoholic dispersions, optionally with other pharmaceutical adjuvants, can be used in the development of controlled and/or sustained release topical cream, lotion, and spray products. Such dispersions can also be cast to develop transdermal patches, and can be sprayed or freeze dried to produce a wide range of structural properties form many cosmetics, agricultural, and pharmaceutical applications. The powdered material can be used as direct compression excipient (e.g., as a binder, diluent, and /or disintegrant) in developing solid dosage forms such as tablets, capsules, etc.

The preparation of oxidized cellulose and its applications in the formulations of various specific and preferred cosmetic and pharmaceutical products are illustrated by the following examples, which are not to be construed as limiting.

EXAMPLE 1

Preparation of Oxidized Cellulose

The aqueous sodium hypochlorite solution used in the present invention was purchased from the University of Minnesota Chemical Specialty Laboratories, Minneapolis, Minnesota. It can be prepared by carefully bubbling chlorine gas, equivalent to about 5.3%, by weight, into a freshly prepared and chilled aqueous sodium hydroxide solution, with a concentration equivalent to about 7.9% (w/v). Since the reaction of chlorine with sodium hydroxide proceeds with the evolution of heat, it is important that the bubbling rate of the chlorine gas be maintained such that the temperature of the reaction medium does not exceed 27° C. The cooling of the sodium hydroxide solution can be achieved by pre-cooling the caustic solution with mechanical refrigeration or cooling water, or by the direct application of ice, or by a combination of these methods. The solution is then slowly brought to room temperature (i.e., to about 25° C.), and then analyzed for the active chlorine content.

One hundred grams of cotton linter, cut into 0.3–0.5 cm × 60 cm strips using a paper shredder, were soaked in about 750 ml of the sodium hypochlorite solution. The reaction mixture was then heated at about 70°–75° C., with occasional stirring, for a period sufficient to render a fine powder of oxidized cellulose product (about 3–4 hours). The white solid was filtered and then washed first with an aqueous solution of sodium thiosulfate (about 1%) and then with water until filtrate showed a near neutral pH. The wet cake suspended in an appropriate volume, preferably about 1:1.5–3 weight-by-volume ratio of acetone or methanol using a mechanical stirrer, and was filtered. The process was repeated three-to-four times to ensure complete depletion of water from the product. The dehydrated oxidized cellulose product, thus obtained, was air dried, and then ground to a particle size of less than 45–50$\mu$. The yield was 70–75%.

EXAMPLE 2

Aqueous Colloidal Dispersions

The dried or wet (before washing with acetone) oxidized cellulose product, prepared according to the procedure of Example 1, was placed in a beaker, and appropriate amounts of water (determined based on the percentage of oxidized cellulose dispersion desired), methyl paraben and propyl paraben (preferably, equivalent to about 0.15% and 0.10%, respectively) were added. The mixture was homogenized using either a high-shear mixer or a household blender, until a stable, uniform homogeneous dispersion was formed. The dispersion was stored in a screw-cap glass bottle.

EXAMPLE 3

Anti-acne Cream

A. Forty grams of the 25% oxidized cellulose dispersion, prepared according to the procedure of Examples 1 and 2, was suspended in 34.5 ml of water. Five hundred milligrams of Carbomer 934P (B. F. Goodrich, Cleveland, Ohio) was then added. Once the carbomer was completely dissolved, 0.09 grams of methyl paraben, 0.06 grams of propyl paraben, 14.3 grams of 70% benzoyl peroxide, and 10 grams of glycerin, were added in the order given. The mixture was stirred for an hour and then homogenized using a hand homogenizer. About 0.5 grams of triethanolamine was then added. An immediate increase in the viscosity of the dispersion occurred. Further stirring for an hour, followed by homogenization of the mixture gave a cosmetically elegant cream product which rubs very smoothly into the skin, and dries rapidly to form a uniform, flexible non-oily, transparent and non-tacky film.

B. Ten grams of powdered oxidized cellulose, prepared according to the procedure of Example 1, was wetted in 55.2 grams of water and then subjected to higher shearing mixing to produce a dispersion. To the resulting dispersion, 5.0 grams of hydroxypropylcellulose was added and the mixture was stirred. Once the hydroxypropylcellulose was dissolved, 2.5 grams of Tween 20, 12.5 grams of glycerin, 0.3 grams of methyl paraben, 0.2 grams of propyl paraben, and 14.3 grams of 70% benzoyl peroxide were added, in the order written.

The mixture was stirred for an additional hour and then homogenized to produce a cream product that showed the attractive properties exhibited by the product prepared according to procedure A of this example.

EXAMPLE 4

Anti-acne Lotion

The same procedures as described in Example 3 were used in the preparation of anti-acne lotion products. The product prepared according to the procedure of Example 3A contained oxidized cellulose dispersion 20 grams (corresponds to about 5% oxidized cellulose content); Carbomer 934P 0.25%, methyl paraben 0.15%, propyl paraben 0.10%, glycerin 10.0% benzoyl peroxide 10.0%, triethanolamine 0.25–0.50%, and water to 100%.

The composition of the product 881-F3 prepared according to the procedure of Example 3B was: powdered oxidized cellulose 5%, hydroxypropylcellulose 5%, Tween 20 2%, methyl paraben 0.3%, propyl paraben 0.2%, glycerine 10%, 70% benzoyl peroxide 14.3%, and water to 100%.

EXAMPLE 5

Microbiological Evaluation of Anti-acne Products

Product 881-F2, a cream product prepared according to the procedure of Example 3B, and product 881-F3, a lotion product described in Example 4, were tested against *Propionibacterium Acnes*. This organism is most implicated in inflammatory acne. Clearasil®, a commercial lotion product marketed by Richardson-Vicks, was used as a control in the study. All contained 10% benzoyl peroxide as an active ingredient. The culture used for growing *P. Aches* was sheep blood agar. Each test plate was inoculated with the organism by dipping a sterile cotton bud in the culture suspension and then streaking it over the surface of the media. About 350 mg of the formulation was placed at the center of the plate on top of the media. The plates were covered and placed, inverted, in an anaerobic jar. Ten milliliters of water were added to a hydrogen/carbon dioxide generator envelope (Gas Pak) and the envelope was placed in the jar. An anaerobic indicator, which remains white under anaerobic conditions but turns blue under aerobic conditions, was also placed in the jar. The jar quickly sealed and incubated at 32° C. Each product was evaluated in duplicate.

The test plates of all three products showed growth of microorganisms, but there were distinct zones of inhibition around the formulation where no growth occurred. The inhibition zone around products 881-F2 and 881-F3 appeared wider than around Clearasil®. The results show that both products 881-F2 and 881-F3 are at least as effective as the commercial Clearasil® lotion product, in their ability to release benzoyl peroxide and suppress *P. acnes*.

EXAMPLE 6

Sunscreen Spray (A) Aqueous based. Twenty grams of the 25% aqueous oxidized cellulose dispersion and 3.0 grams of Tween 20 were weighed directly in a beaker and about 59 ml of water was added. The mixture was stirred. To the homogeneously dispersed mixture, 0.12 grams of methyl paraben, 0.08 grams of propyl paraben, 7.0 grams of octyldimethylaminobenzoic acid (Escalol 705), 3.0 grams of oxybenzone (UV-9), 0.1 grams of hydroxyethylcellulose K-100 LV and 7.0 grams of glycerin, were added in the order written. The stirring was continued for about an hour more. The product was then homogenized and stored in a polyethylene spray bottle.

(B) Hydro-alcoholic System. The same procedure as described in Example 5A was used. The only exception was that a 1:1 ratio of ethanol and water, by weight, was utilized, instead of water, as the dispersing medium. Physically stable and cosmetically elegant products result in both cases.

EXAMPLE 7

Anti-fungal Cream

The same procedure as described in Example 3B was used for the preparation of an anti-fungal cream product 883-F11. The only difference was that an aqueous solution of hydroxypropylcellulose was used instead of powder. It contained 15% oxidized cellulose, 7.5% hydroxypropylcellulose (Klucel ® EF), 2.5% Tween 20, 7.5% glycerin, 0.3% methyl paraben, 0.2% propyl paraben, 1% tolnaftate, and 66% water.

The anti-fungal activity of the product was evaluated against *Trichophyton rubrum* and *T. mentagrophyte*. These microorganisms are frequently associated with athletes' foot infections. The media used was sabroud Agar plate. Tinactin ® (Schering Corporation) was used as a control product. The fungi were dispersed in water and two drops of the dispersion were placed on each plate. Filter paper discs impregnated with the product, equivalent to about 0.30-5 g of tolnaftate, were then placed on the plates that had been inoculated with the fungi. Unimpregnated filter paper discs were also placed on separate inoculated plates to serve as a blank to make sure the media supports the growth of fungi. The plates were covered and incubated at room temperature. The tests were run in duplicate. Pictures of the test plates were taken after 11 days of incubation. The results clearly show that the test product is more potent than Tinactin ® against other microorganisms.

The substantivity of the product was determined by the sock transfer test. Tinactin ® was used as a control. Four subjects were used in the study. Each subject was given a new pair of "Men's Cushion" socks (80% cotton and 20% rayon), and asked to wear tennis shoes during the test period (4 hours). The application procedure involved rubbing-in an accurately weighed quantity (0.35-0.45 g) of the product and Tinactin ® on the right and left feet, respectively, by the subjects using the tip of a clean finger for each sample. On all subjects, the test product dried within 5 minutes after application, whereas Tinactin ® remained greasy. The subjects then put on their socks and shoes and went about their normal activities. Each subject waited for 12-15 minutes before wearing socks. After the four hours test period, the socks were collected and appropriately labeled. Tolnaftate was then extracted from each sock using acetonitrile, and the amount of drug extracted was quantified by the HPLC method using testosterone as an internal reference.

For extracting tolnaftate, the sock was hung from a clamp, and washed with about 150 ml of acetonitrile. The washed solvent, which was collected in a beaker, was filtered into a 250 ml volumetric flask using glass wool. The sock was then immersed and swirled in 50-75 ml of acetonitrile. After removing the sock, the solvent was filtered into the same volumetric flask used previously. An appropriate amount of testosterone dissolved in the same solvent was added to the combined acetonitrile wash. Washing of the sock was then continued until the solvent in the volumetric flask filled the flask to the designated mark. Twenty microliters of this solution was used in this analysis. The HPLC conditions used were: column: microbodapak $C_{18}$ analytical; mobile phase: methanol:water (3:1); flow rate: 1 ml/min.; wavelength: 255 nm. The retention times for the tolnaftate and testosterone were about 4 minutes and 8 minutes, respectively. The results of recovery of tolnaftate from the sock, when an accurately weighed amount of 883-F11 and Tinactin ® were applied directly on the socks, using acetonitrile as the extracting solvent, are presented in Table 1. Table 2 lists the results of the substantivity test. The data in Table 1 show 100% recovery of tolnaftate from the sock treated with product 883-F11, whereas in the case of Tinactin ® the recovery was about 94.4%. The results of Table 2 clearly show that the product of this invention is very substantive compared to Tinactin ®; the amount of tolnaftate transferred to the socks ranged from 5.63% to 11.93% for product 883-F11 vs. 32.36% to 69.50% for Tinactin ®.

TABLE 1

Percent Recovery of Tolnaftate from the Sock

| Product[a] | Amt Applied | % Tolnaftate Recovered |
|---|---|---|
| 883-F11[a] | 0.4343 | 100.22 |
|  | 0.4207 | 99.78 |
|  |  | Avg. = 100.00 |
| Tinactin ®[a] | 0.4116 | 93.96 |
|  | 0.4216 | 94.81 |
|  |  | Avg. = 94.38 |

[a]Product 883-F11 and Tinactin contained 1.07% and 1.01% tolnaftate, respectively.

TABLE 2

Results of the Substantivity Test

| Subject i.d. | Product[a] | Amt. Applied (g) | % Tolnaftate absorbed on the sock |
|---|---|---|---|
| VK | Tinactin | 0.4455 | 69.50 |
|  | 883-F11 | 0.4491 | 9.61 |
| GA | Tinactin | 0.3610 | 86.30 |
|  | 883-F11 | 0.3670 | 5.63 |
| VS | Tinactin | 0.4329 | 32.36 |
|  | 883-F11 | 0.4566 | 11.93 |
| MA | Tinactin | 0.4269 | 46.80 |
|  | 883-F11 | 0.4089 | 6.88 |

[a]Product 883-F11 and Tinactin contained 1.07% and 1.01% tolnaftate, respectively.

The present product when applied on the skin dries rapidly to form uniform, flexible, non-tacky, and non-oily films, whereas Tinactin ® remains oily, and thereby readily transfers onto the sock.

EXAMPLE 8

Evaluation of Oxidized Cellulose as a Direct Compression Excipient

An oxidized cellulose product, prepared according to the procedure of Example 1, was ground to a particle size of less than 425 mµ. Tablets were prepared by mixing the ingredients listed in Table 3 in the indicated ratio, followed by compressing using a Carver hydraulic press at a pressure of 2000 lb. with a 30 second dwell time. Each tablet weighed 500±10 mg.

TABLE 3

| Ingredient | Composition % | mg/tablet |
|---|---|---|
| Oxidized cellulose | 20.0 | 90.0 |
| Lactose NF (Fast-Flo) | 79.0 | 355.5 |
| Magnesium Stearate | 1.0 | 4.5 |

The hardness of the tablet was evaluated using a Strong Cobble Hardness Tester. For measuring the water penetration rate, the tablet was placed on a flat horizontal surface on a laboratory jack. A 2 μl disposable micropipette was held in a vertical position above surface of the tablet. The pipette was then filled with water by capillary action. The tablet was then slowly raised to the point where it touched the end of the capillary. As soon as the tablet touched the capillary, the water started penetrating into the tablet. The time for the water to drain into the tablet was recorded with a stop watch. This was used in the determination of the water penetration rate. The disintegration times of the tablets were measured using the USP disintegration apparatus. The results are presented in Table 4.

TABLE 4

|  | Number of Tablets Tested | Average value |
|---|---|---|
| Hardness | 3 | 5.17 kg |
| Water Penetration Rate | 6 | 10.49 mg/sec |
| Disintegration Time | 6 | 30 seconds |

What is claimed is:

1. A method of oxidizing a cellulose material into an oxidized cellulose product, comprising:
   treating the cellulose material with a hypochlorite solution having an active chlorine content of between about 4 and about 6%, at a pH exceeding 9.5 and at a temperature, and for a time, effective to convert the cellulose material into the oxidized cellulose product;
   filtering the oxidized cellulose product; and
   washing the oxidized cellulose product to remove chlorine and to raise the oxidized cellulose product to a neutral pH.

2. A method in accordance with claim 1 wherein the oxidized cellulose product is additionally rinsed with methanol or acetone.

3. A method in accordance with claim 2 wherein the oxidized cellulose product is washed with an antichlor agent to remove chlorine therefrom.

4. A method in accordance with claim 3 wherein the effective pH ranges from about 9.5 to about 14.

5. A method in accordance with claim 4 wherein the initial pH of the hypochlorite solution is about 13.5 to 14.

6. A method in accordance with claim 4 wherein the effective temperature ranges from about 25° to about 90° C.

7. A method in accordance with claim 4 wherein the effective temperature ranges from about 70° to about 80° C.

8. A method in accordance with claim 6, wherein the volume to volume ratio of cellulose solution is about 1:>5.

9. A method in accordance with claim 6, wherein the weight to volume ratio of cellulose to hypochlorite ranges from about 1:7.5 to about 1:15.

10. A method in accordance with claim 6 wherein the cellulose material is cotton linters, α-cellulose, wood cellulose, or purified wood cellulose.

11. A method in accordance with claim 10 wherein the pH of the reaction mixture exceeds 9.5 throughout the oxidation step.

12. A method in accordance with claim 3 wherein the antichlor agent is sodium thiosulfate.

13. A method of oxidizing a cellulose material into an oxidized cellulose product, comprising:
   reacting the cellulose material with a hypochlorite solution having an active chlorine content of between about 4% and 6%, at a temperature ranging from about 60° C. to about 80° C., and a pH ranging from about 9.5 to about 14 for a period of time effective to convert the cellulose material into the oxidized cellulose product;
   isolating the oxidized cellulose product by filtration;
   washing the oxidized cellulose product in an aqueous solution of an antichlor agent;
   followed by rinsing the oxidized cellulose product with methanol or acetone.

14. A method in accordance with claim 13 wherein the pH of the reaction mixture exceeds 9.5 throughout the oxidation step.

15. A method in accordance with claim 13 wherein the cellulose material is cotton linters, α-cellulose, wood cellulose, or purified wood cellulose.

16. A method in accordance with claim 15, wherein the volume of hypochlorite is at least 5 times the weight of cellulose.

17. A method in accordance with claim 15, wherein the weight to volume ratio of cellulose to hypochlorite ranges from about 1:7.5 to about 1:15.

18. An oxidized cellulose product made in accordance with the process of claim 1.

19. An oxidized cellulose product made in accordance with the process of claim 4.

20. An oxidized cellulose product made in accordance with the process of claim 13.

21. An oxidized cellulose product made in accordance with the process of claim 15.

* * * * *